United States Patent [19]

Jernow et al.

[11] 4,000,182

[45] Dec. 28, 1976

[54] SYNTHESIS OF CYCLOPENTANOL

[75] Inventors: Jane Liu Jernow, Verona; Perry Rosen, North Caldwell, both of N.J.

[73] Assignee: Hoffmann-La Roche Inc., Nutley, N.J.

[22] Filed: Aug. 14, 1975

[21] Appl. No.: 604,522

Related U.S. Application Data

[62] Division of Ser. No. 508,131, Sept. 23, 1974, Pat. No. 3,931,234, which is a division of Ser. No. 457,528, April 3, 1974, Pat. No. 3,855,250, which is a division of Ser. No. 317,589, Dec. 22, 1972, abandoned.

[52] U.S. Cl. ......................................... 260/468 K
[51] Int. Cl.² ......................................... C07C 69/74
[58] Field of Search .............................. 260/468 K

[56] References Cited

UNITED STATES PATENTS

| | | | |
|---|---|---|---|
| 3,558,682 | 1/1971 | Pappo | 260/468 |
| 3,832,380 | 8/1974 | Matsui | 260/468 |

*Primary Examiner*—Robert Gerstl
*Attorney, Agent, or Firm*—Samuel L. Welt; Bernard S. Leon; William H. Epstein

[57] ABSTRACT

Process for synthesizing the lactone, (dl) 3,3a beta-4,5,6,6a beta-hexahydro-4beta(3-hydroxy-1-trans-octenyl)-5α-hydroxyl-2-oxo-2H-cyclopenta [b] furan, a known intermediate for producing prostaglandin $F_2$ and $F_{2\alpha}$ from dihydroresorcyclic acid, and intermediates in this process.

1 Claim, No Drawings

SYNTHESIS OF CYCLOPENTANOL

CROSS REFERENCE TO RELATED APPLICATIONS

This application is a divisional of U.S. application Ser. No. 508,131, Jernow et al., filed Sept. 23, 1974, now U.S. Pat. No. 3,931,234, Jan. 6, 1976 which in turn is a divisional application of U.S. application Ser. No. 457,528, filed Apr. 3, 1974, Jernow et al. now U.S. Pat. No. 3,855,250, Dec. 17, 1974 which in turn is a divisional of U.S. application Ser. No. 317,589 filed Dec. 22, 1972 now abandoned.

BACKGROUND OF THE INVENTION

Prostaglandins are well known therapeutic agents. For example, prostaglandin $F_{2\alpha}$ is a well known agent for inducing labor in pregnant women and for the therapeutic termination of pregnancy.

In an article by Corey et al. entitled "Stereo Controlled Synthesis of Prostaglandin $F_{2\alpha}$ and $E_2$ (dl)", *Journal of American Chemical Society*, Vol., 91, pp. 5675–5678 (1969), the synthesis of various prostaglandings such as $F_2$ and $F_{2\alpha}$ from (dl) 3,3a beta-4,5,6,6a beta-hexahydro-4beta(3-hydroxyl-1-trans-octenyl)-5α-hydroxyl-2-oxo-2H-cyclopenta[b]furan, which has the formula:

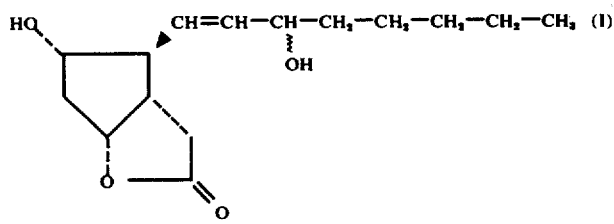

is disclosed.

SUMMARY OF THE INVENTION

In accordance with this invention, a new synthesis for the lactone of formula I has been discovered starting from dihydroresorcyclic acid, which has the formula:

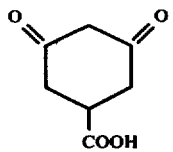

via an intermediate of the formula:

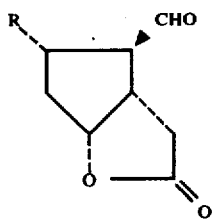

wherein R is hydroxy protected with a hydrolyzable ether or ester group.

DETAILED DESCRIPTION OF THE INVENTION

As used throughout this application, the term "lower alkyl" includes both straight chain and branched chain alkyl groups having from 1 to 7 carbon atoms, such as methyl, ethyl and propyl, preferably methyl. As used herein, the term "lower alkoxy" comprehends groups having from 1 to 7 carbon atoms such as methoxy and ethoxy. As also used herein, the term "lower alkanoic acids" comprehends an alkanoic acid of 2 to 7 carbon atoms such as propionic acid and acetic acid. As further used herein, the term "halogen"or "halo", unless otherwise stated, comprehends fluorine, chlorine, bromine and iodine.

In the process of this invention, all compounds having one or more asymmetric carbon atoms can be produced as racemic mixtures. These racemic mixtures which are obtained can be resolved at the appropriate steps in the process of this invention by methods well known in the art discussed more fully below, whereupon subsequent products may be obtained as the corresponding optically pure enantiomers.

In the pictorial representation of the compounds given throughout this application, a thickened tapered line (▼) indicates a substituent which is in the β-orientation (above the plane of the molecule), a dotted line (---) indicates a substituent which is in the α-orientation (below the plane of the molecule) and a wavy line (∿) indicates a substituent which is in either the α- or β-orientation. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, tolyl, etc., which can be unsubstituted or substituted in one or more positions with a lower alkylenedioxy, a halogen, a nitro, a lower alkyl or a lower alkoxy substitutent, and polynuclear aryl groups such as naphthyl, anthryl, phenanthryl, azulyl, etc., which can be substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl. The term "aryl lower alkanoic acid" comprehends acids wherein aryl and "lower alkanoic acid" are as defined above, particularly benzoic acid.

As still further used herein, the term "carboxy protected with a group convertible thereto by hydrolysis" comprehends any conventional organic acid protecting group which can be removed by hydrolysis. The preferred organic acid protecting groups are the esters.

Any conventional ester that can be hydrolyzed to yield the acid can be utilized as the protecting group. Exemplary esters useful for this purpose are alkyl esters, particularly aroic esters, particularly phenyl ester and the aryl lower alkyl esters, particularly benzyl ester.

As used herein, the term "hydrolyzable ester or ether group" designates any ester or ether which can be hydrolyzed to yield the hydroxy group. Exemplary ester groups useful for this purpose are those in which the acyl moiety is derived from a lower alkanoic, an aryl lower alkanoic, or a lower alkane dicarboxylic acid. Among the acids which can be utilized to form such ester groups are the acid anhydrides and the acid halides, preferably chlorides or bromides, with the lower alkanoic acid anhydrides, e.g., acetic anhydride and caproic anhydride, the aryl lower alkanoic acid anhydrides, e.g., benzoic acid anhydrides, lower alkane dicarboxylic acid anhydrides, e.g., succinic anhydride, and chloroformates, e.g., trichloroethylchloroformate, being preferred. A suitable ether protecting group is, for example, the tetrahydropyranyl ether or 4-methoxy-5,6-dihydro-2H-pyranyl ether. Others are arylmethyl ethers such as benzyl, benzhydryl, or trityl ethers or α-lower alkoxy lower alkyl ether, for example, methoxymethyl or allylic ethers, or alkyl silyl ethers such as trimethyl silyl ether.

In accordance with the process of this invention, the compound of formula III can be obtained from dihydroresorcyclic acid (II) according to the following reaction scheme:

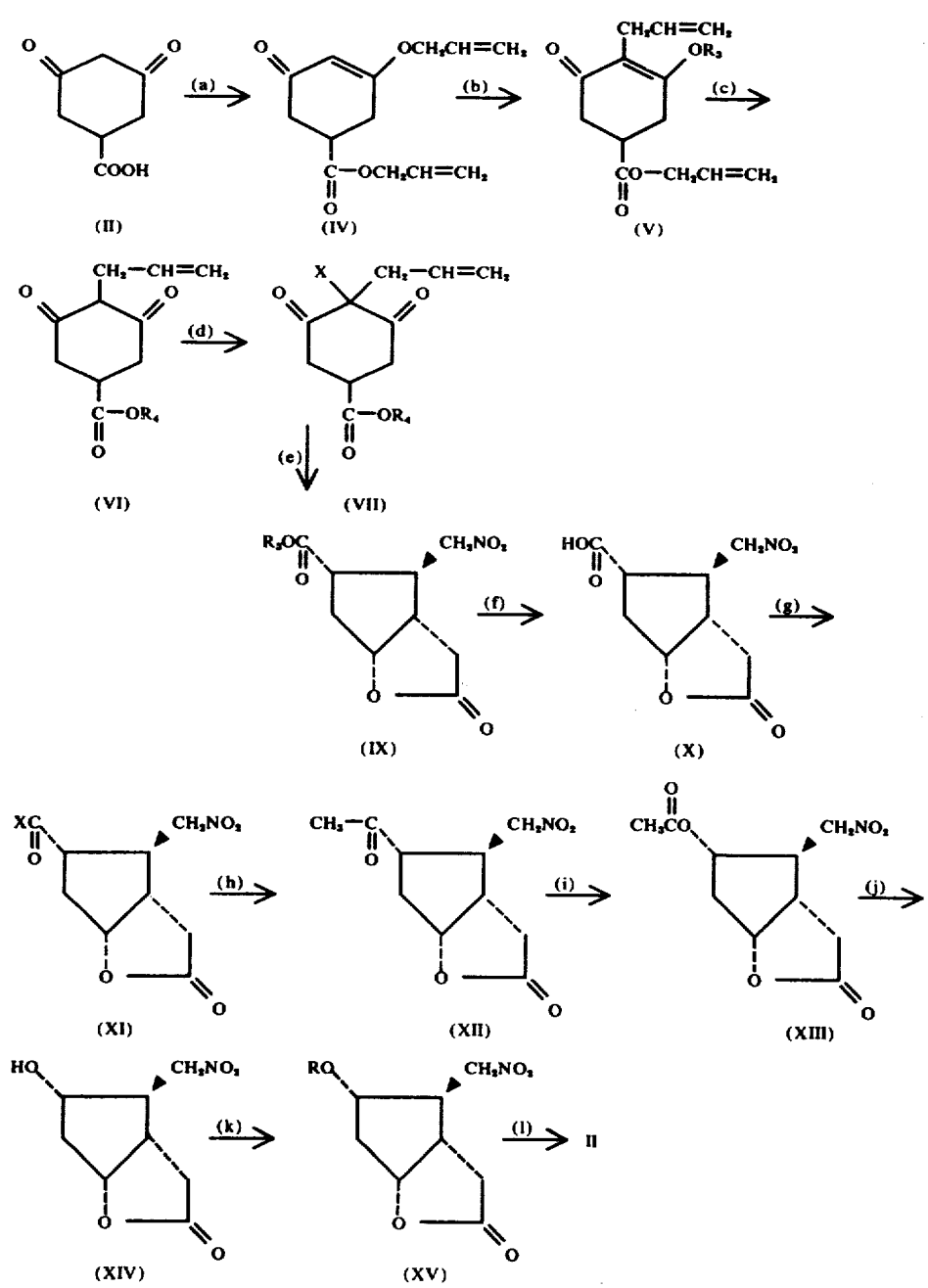

wherein $R_1$ is hydrogen or lower alkyl; $R_3$ is lower alkanoyl; $R_4$ is lower alkyl; X is halogen; and R is as above.

In the first step, i.e., reaction step (a) of the reaction sequence of this invention, the compound of formula II is reacted with an alcohol of the formula:

$$HO-CH_2-CH=CH_2 \qquad XX$$

The compound of formula IV is prepared by reacting the compound of formula II with a compound of the formula XX. In carrying out this reaction, any conventional method of esterification can be utilized. However, in this case, at least 2 moles of the compound of formula XX is utilized per mole of the compound of formula II. Generally, it is preferred to utilize from about 2 to 20 moles of the compound of formula XX per mole of the compound of formula II. However, if desired, larger molar quantities of the compound of the formula XX can be utilized per mole of the compound of formula II without any deleterious effects. In carrying out this reaction, any of the conditions conventional in esterifying acids with alcohols can be utilized. Among the preferred reaction conditions in carrying out the reaction of step (a), in the presence of an acid catalyst, any conventional acid catalyst such as p-toluene sulfonic acid can be utilized. Furthermore, any of the inert organic solvents conventional in esterification procedures can be utilized in carrying out this reaction. Among the preferred solvents are the aromatic solvents such as benzene and toluene. In carrying out this reaction, temperatures and pressures are not critical and the reaction can be carried out at room temperature, i.e., 20° centigrade. However, it is generally preferred to carry out this reaction at the reflux temperature of the reaction medium.

The compound of formula IV is converted to the compound of formula V by treating the compound of formula IV with an anhydride of a lower alkanoic acid. In carrying out this reaction, the lower alkanoic acid anhydride can act as the reaction medium. Therefore, it is generally desired to utilize excess lower alkanoic acid anhydrides in this reaction. Any conventional lower alkanoic acid anhydride can be utilized in carrying out the reaction of step (b). Among the preferred lower alkanoic acid anhydrides are acetic acid anhydride and propionic acid anhydride. Generally, this reaction is carried out at a reflux temperature of the reaction medium.

The compound of formula V is converted to the compound of formula VI by treating the compound of formula V with an alkali metal alkoxide, preferably an alkali metal methoxide. In carrying out this reaction, any alkali metal alkoxide can be utilized. Among the preferred alkali metal alkoxides are lithium methoxide, sodium methoxide and potassium methoxide. In carrying out this reaction, a lower alkanol is utilized as the solvent. Any conventional lower alkanol such as methanol, ethanol, isopropanol, etc. can be utilized as the organic solvent medium. In carrying out this reaction, temperature and pressure are not critical and this reaction can be carried out at room temperature and atmospheric pressure. On the other hand, higher or lower temperatures can be utilized. Generally it is preferred to carry out this reaction at a temperature of from -25° centigrade to 30 degrees centigrade.

The compound of formula VI is converted to the compound of formula VII by halogenating the compound of formula VI. Any conventional halogenating agent can be utilized to carry out this conversion. Generally, it is preferred to utilize chlorinating or brominating agents in carrying out this conversion. Among the preferred chlorinating agents are chlorine dissolved in a chlorinated hydrocarbon, tert-butylhypochlorite, and N-chlorosuccinimide, particularly, tert-butylhypochlorite. Among the preferred brominating agents are included bromine dissolved in a halogenated hydrocarbon or N-bromosuccinimide. This reaction can be carried out in an inert organic solvent. In carrying out this reaction, any conventional inert organic solvent can be utilized such as the halogenated hydrocarbons, the lower alkanols, diethyl ether and tetrahydrofuran. In carrying out this reaction, temperature and pressure are not critical, and in general, the reaction can be carried out at room temperature and atmospheric pressure. In carrying out this reaction, temperatures of from about −50° centigrade to about 100° centigrade are generally utilized with temperatures of from 40° centigrade to 60° centigrade being particularly preferred.

The compound of formula VII is converted to the compound of formula IX by the procedure disclosed in U.S. patent application Ser. No. 300,633, Rosen et al., filed Oct. 25, 1972. Therefore, the reaction of step (e) is carried out utilizing the intermediates designated in Ser. No. 300,633 as VIII, IX, X, XI, XI-A and XII, wherein $R_{30}$ is a nitro methyl group. This conversion is described in Examples 3 through 9 of U.S. patent application Ser. No. 300,633.

The compound of formula IX is converted to the compound of formula X by hydrolysis. Any conventional method of ester hydrolysis can be utilized to convert the compound of formula IX to the compound of formula X. The compound of formula X can be converted to the compound of formula XI via reaction step (g). The reaction of step (g) is carried out by any of the conventional methods for forming an acid halide from the corresponding acid. Any method conventional in halogenating acids can be utilized in carrying out the reaction of step (g). Among the preferred methods of halogenating the compound of formula X is by treating this compound with a halogenating agent, preferably a chlorinating agent such as oxalyl chloride, thionyl chloride, phosphorous pentachloride, etc. Any conventional halogenating agent can be utilized in carrying out this reaction. Any of the conditions conventional in utilizing these halogenating or chlorinating agents cen be utilized in carrying out the reaction of step (g).

The compound of formula XI is converted to the compound of formula XII via reaction step (h) by treating the compound of formula XI with a methylating agent. Any conventional methylating agent can be utilized in carrying out this reaction. Among the preferred methylating agents are dimethyl zinc, lithium, dimethyl copper, dimethyl cadmium. In carrying out this reaction, any conventional inert organic solvent can be utilized as the reaction medium. Among the preferred inert organic solvents are included hydrocarbon solvents such as benzene, toluene, xylene, etc., and chlorinated hydrocarbons such as carbon tetrachloride, methylene chloride, etc. In carrying out this reaction, temperature and pressure are not critical and this reaction can be carried out at room temperature and atmospheric pressure. If desired, higher or lower temperatures and pressures can be utilized.

The compound of formula XII is converted to the compound of formula XIII, via reacton step (i), by treating the compound of formula XII with a peracid. Any conventional peracid, preferably a perorganic acid such as perbenzoic acid, m-chloroperbenaoic acid, peracetic acid, pertrilfuoroacetic acid, etc., can be utilized in carrying out this reaction. Generally this reaction is carried out in the presence of an inert organic solvent. Any conventional inert organic solvent can be utilized in carrying out this reaction. Among the preferred inert organic solvents are included the halogenated hydrocarbon solvents such as methylene chloride, chloroform, ethylene chloride, etc. In carrying out this reaction, temperature and pressure are not critical and this reaction can be carried out at room temperature and atmospheric pressure. In general, it is preferred to carry out this reaction at from about −20° centigrade to +60° centigrade. In carrying out this reaction, any conventional perorganic acid can be utilized such as the aromatic perorganic acids such as p-nitroperorganic acid, perbenzoic acid, m-chloroperbenzoic acid, and the aliphatic perorganic acids such as peracetic acid, trifluoroperacetic acid, etc.

The compound of formula XIII is converted to the compound of formula XIV via reaction step (j) by hydrolyzing the compound of formula XIII. Any conventional method of ester hydrolysis can be utilized to convert the compound of formula XIII to the compound of formula XIV.

The compound of formula XIV is converted to the compound of formula XV by either esterifying or etherifying the free hydroxy group with a hydrolyzable ether or ester protecting group. The esterification or etherification can be carried out by conventional esterification or etherification procedures. Among the preferred hydrolyzable ester groups are lower alkanoyloxy with p-phenylbenzoyl being especially preferred. In the case where acetoxy is utilized, the compound of formula XV will be the compound of formula XIII since there is no necessity to hydrolyze the compound of formula XIII to produce a compound of formula XIV and then reesterifying the compound of formula XIV. Among the preferred hydrolyzable ether groups are included tetrahydropyranyl.

The compound of formula XV is converted to the compound of formula II by oxidizing the compound of formula XV with an oxidizing agent which selectively oxidizes a nitromethyl group to an aldehyde. The preferred oxidizing agents are the permanganate oxidizing agents with alkali metal permanganates such as sodium permanganate being particularly preferred. In carrying out this reaction, the compound of formula XV is converted to its aci-nitro salt before treatment with permanganate.

The compound of formula XV can be converted to its aci-nitro salt by treatment with an alkali metal lower alkoxide, preferably lithium methoxide. In carrying out this reaction, temperature and pressure are not critical, and in general, the reaction can be carried out at room temperature and atmospheric pressure. This reaction can be carried out in an inert organic solvent. In this reaction, any conventional inert organic solvents may be utilized. Among the preferred solvents are any of the solvents mentioned hereinbefore with methanol being especially preferred.

The oxidation of the aci-nitro salt of the compound of formula XV can be carried out in the presence of an inert organic solvent or water. In this reaction, any conventional inert organic solvent may be utilized such as tetrahydrofuran, dioxane, acetone, diglyme or a lower alkyl ether. In carrying out this reaction, temperature and pressure are not critical and this reaction can be carried out at room temperature and atmospheric pressure. In general, it is preferred to carry out this reaction at a temperature of from about −10° centigrade to about 75° centigrade with a temperature of about 0° centigrade being particularly preferred.

The compound of formula III is converted to the compound of the formula:

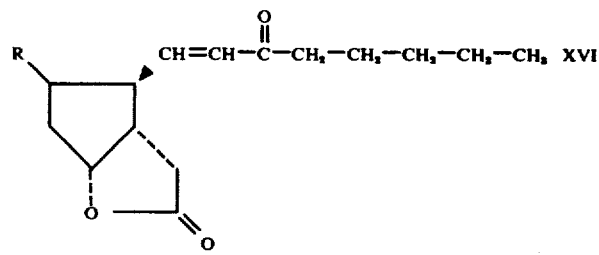

wherein R is as above;
by treating the compound of formula III with either a phosphorane of the formula:

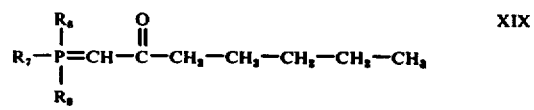

wherein $R_7$, $R_8$ and $R_9$ are aryl;
or a phosphonate of the formula:

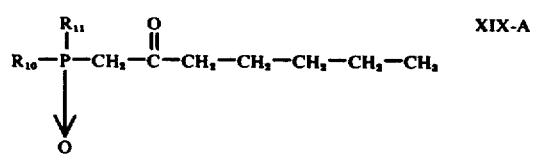

wherein $R_{10}$ and $R_{11}$ are aryloxy or lower alkoxy.

The reaction of a phosphorane of formula XIX with the compound of formula III can, if desired, be carried out in the presence of an inert organic solvent, In carrying out this reaction, any conventional inert organic solvent can be utilized. Among the conventional inert organic solvents which can be utilized in accordance with this invention are included benzene, toluene, N,N-dimethylformamide, tetrahydrofuran, 1,2-dimethoxyethane and dioxane. In carrying out this reaction, temperature and pressure are not critical, and this reaction can be carried out at from about 50° centigrade to about 150° centigrade and atmospheric pressure.

The phosphoranes of formula XIX above can be prepared by known procedures from the corresponding phosphonium salts. In accordance with this invention, $R_7$, $R_8$ and $R_9$ can be any conventional aryl group. The aryl groups which may form the substituent designated by $R_7$, $R_8$ and $R_9$ include mononuclear aryl groups such as phenyl or substituted phenyl such as tolyl, xylyl, mesityl, 4-methoxyphenyl, etc. The aryl substituent can be a polynuclear aryl group such as naphthyl, anthryl, phenanthryl, azylyl, etc.

The reaction between the phosphonate of formula XIX-A and the compound of formula II can be carried out by first providing a solution of an alkali metal base and the phosphonate of formula XIX-A in an inert organic solvent and then adding the compound of formula III to this reaction mixture. In carrying out this reaction, any conventional alkali metal base can be utilized, such as the alkali metal hydrides such as sodium hydride and alkyl lithium; alkali metal lower alkoxides such as sodium methoxide and sodium ethoxide; and the alkali metal amide bases such as sodamide, potassium amide, as well as other alkali metal lower alkyl amides. In carrying out this reaction, any conventional inert organic solvent can be utilized such as benzene, toluene, N,N-dimethylformamide, tetrahydrofuran, dioxane,1,2-dimethoxyethane. In carrying out this reaction, a temperature of from 0° centigrade to the reflux temperature can be utilized.

The phosphonate of formula XIX-A can be substituted by alkoxy or aryloxy groups. As with $R_7$, $R_8$ and $R_9$ in the phosphorane of formula XIX, the aryloxy groups denoted by $R_{10}$ and $R_{11}$ in the phosphonate of the formula XIX-A can contain mononuclear or polynuclear aryl groups which may be substituted or unsubstituted. When the compound of formula XIX-A is substituted by alkoxy groups, it is generally preferred to utilize alkoxy groups containing from 1 to 4 carbon atoms such as methoxy, ethoxy and isopropyl. Among the aryloxy groups, phenoxy groups which are singly or multiply substituted with a lower alkyl, nitrogen, halogen, lower alkoxy or dialkylamino group are generally preferred.

In accordance with this invention, the compound of formula XVI is next converted to a compound of the formula:

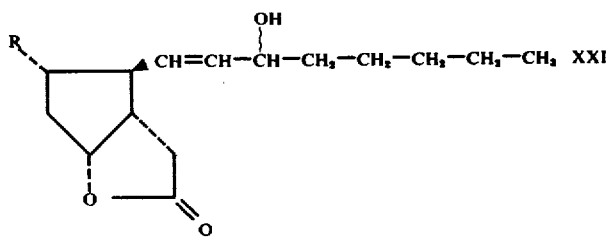

wherein R is as above.

The compound of formula XXI can be obtained by treating the compound of formula XVI with a reducing agent. In carrying out this reaction, any conventional reducing agent which will selectively reduce a keto group to a hdyroxy group can be utilized. Preferred reducing agents are the hydrides, particularly the aluminum hydrides, such as the alkali metal aluminum hydrides, and the borohydrides, such as the alkali metal borohydrides and zinc borohydride. In carrying out this reaction, temperature and pressure are not critical, and the reaction can be carried out at room temperature and atmospheric pressure or at elevated or reduced temperatures and pressures. Generally, it is preferred to carry out this reaction at a temperature of from −10° centigrade to the reflux temperature of the reaction mixture. This reduction reaction can be carried out in the presence of an inert organic solvent. Any conventional inert organic solvent or water can be utilized in carrying out this reaction, such as the conventional, inert organic solvents hereinbefore mentioned. Among the preferred solvents are dimethoxy ethylene glycol and ethers such as tetrahydrofuran, diethyl ether and dioxane.

If desired, the compound of formula XXI can be hydrolyzed to form the compound of formula I. Any conventional method of ether or ester hydrolysis can be utilized.

The compound of formulae I or XXI can be separated into its two isomeric forms by conventional means to produce a compound of the formula:

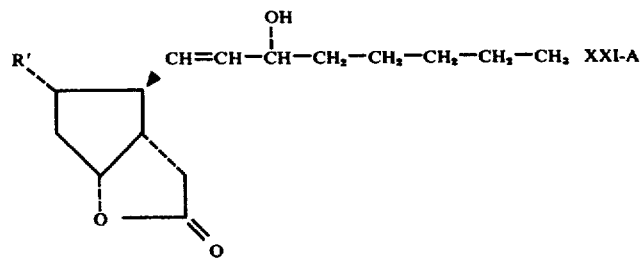

wherein R' is hydroxy or hydroxy protected with a hydrolyzable ether group;
and a compound of the formula:

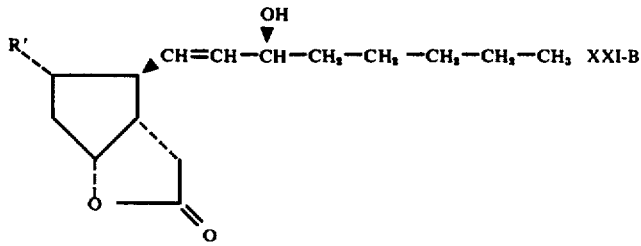

XXI-B wherein R' is as above.

Any conventional means of separation such as column chromatography, vapor phase chromatography, etc., can be utilized to carry out this reaction.

The following examples are illustrative but not limitative of the claimed invention. All temperatures are in degrees centigrade. The ether used is diethyl ether.

EXAMPLE 1

5-(2-Propenylcarbonyloxy)-3-(2-propenyloxy)-2-cyclohexen-1-one

To a solution of 156 g. of dihydroresorcyclic acid in 2 liters of benzene and 580 ml. of allyl alcohol was added 6 g. of p-toluene sulfonic acid monohydrate. The solution was refluxed for 18 hours and the water formed during the reaction was removed by means of a Dean-Stark apparatus. The solution was then washed with a saturated sodium bicarbonate soluton and the organic layer dried (MgSO$_4$). The solvent was then removed under reduced pressure to give 5-(2-Propenylcarbonyloxy)-3-(2-propenyloxy)-2-cyclohexen-1-one.

EXAMPLE 2

3-Acetoxy-2-(2-propenyl)-5-(2-propenylcarbonyloxy)-2-cyclohexen-1-one

A mixture of 200 g. of 5-(2-propenylcarbonyloxy)-3-(2-propenyloxy)-2-cyclohexen-1-one and 500 g. of acetic anhydride was refluxed under argon for 5 hours. The excess acetic anhydride was then removed under reduced pressure and the residue distilled to give 3-acetoxy-2-(2-propenyl)-5-(2-propenylcarbonyloxy)-2-cyclohexen-1-one, b.p. 150/0.1 mmHg.

EXAMPLE 3

Methyl 4-(2-propenyl)-3,5-cyclohexenedione carboxylate

To a solution of 139 g. of 3-acetoxy-2-(2-propenyl)-5-(2-propenylcarbonyloxy)-2-cyclohexen-1-one in 1 liter of dry methanol was added dropwise at 0° centigrade 420 ml. of a 2.4 molar solution of lithium methoxide in methanol. The reaction was run under argon. After 1 hour at 0° centigrade, 4N-aqueous sulfuric acid was slowly added to pH 3 and the methanol removed under reduced pressure. The residue was then extracted with ethyl acetate and the organic solution dried (MgSO$_4$). The solvent was removed under reduced pressure and the residue crystallized from ethyl acetate-petroleum ether to give methyl-4-(2-propenyl)-3,5-cyclohexanedione carboxylate, m.p. 130°–132° centigrade.

EXAMPLE 4

3,3a,beta-4,5,6,6a,beta-hexahydro-4beta-nitromethyl-2-oxo-2H-cyclopenta [b]furan-5alpha-carboxylic acid To a solution of 472 ml. of tetrahydrofuran and 95 ml. of an aqueous solution containing 20% by weight sulfuric acid was added 25 g. of 3,3a,beta-4,5,6,6a,-beta-hexahydro-4beta-nitromethyl-2-oxo-2H-cyclopenta[b]furan-5 alpha-carboxylic acid methyl ester. After refluxing for 48 hours, most of the solvent was removed under reduced pressure and the residue extracted with an aqueous saturated sodium bicarbonate solution. The basic water solution was then extracted with ethyl acetate, the organic layer washed with water and the washing added to the bicarbonate solution. The aqueous solution was then acidified to pH 3 with 4N-aqueous sulfuric acid and the resulting mixture extracted with ethyl acetate. The ethyl acetate solution was dried (MgSO$_4$) and the solvent removed under reduced pressure. Trituration of the residue with ether afforded 3,3a,beta-4,5,6,6a,beta-hexahydro-4beta-nitromethyl-2-oxo-2H-cyclopenta[b]furan-5alpha-carboxylic acid, m.p. 125°–127° centigrade.

EXAMPLE 5

3,3a,beta-4,5,6,6a,beta-hexahydro-4beta-nitromethyl-2-oxo-2H-cyclopenta [b] furan-5alpha-carboxylic acid chloride A mixture of 20 g. of 3,3a,beta-4,5,6,6a,beta-hexahydro-4beta-nitromethyl-2-oxo-2H-cyclopenta [b] furan-5alpha-carboxylic acid and 20 ml of oxalyl chloride was heated at 50° centigrade for 2 hours. The excess oxalyl chloride was then removed under reduced pressure and the residue treated with 50 ml. of hexane. The solvent was then removed under reduced pressure to give 3,3a,beta-4,5,6,6a,beta-hexahydro-4beta-nitromethyl-2-oxo-2H-cyclopenta [b] furan-5alpha-carboxylic acid chloride.

EXAMPLE 6

3,3a,beta-4,5,6,6a,beta-hexahydro-4beta-nitromethyl-5alpha-acetyl-2oxo-2H-cyclopenta [b] furan To 500 ml. of a 0.19 molar solution of dimethyl cadmium in methylene chloride was added 10 g. of 3,3a,-beta-4,5,6,6a,beta-hexahydro-4beta-nitromethyl-2-oxo-2H-cyclopenta [b] furan-5alpha-carboxylic acid chloride dissolved in 50 ml. of methylene chloride. The mixture was stirred for 18 hours and then slowly poured onto 200 g. of ice containing 5 ml. of 96% by weight sulfuric acid in water. The aqueous layer was then saturated with sodium chloride and extracted with ethyl acetate. The organic layers were then combined, dried (MgSO$_4$) and the solvent removed under reduced pressure. The residue was then dissolved in diethyl ether and passed through 55 g. of silica gel to give 9.2 g. of 3,3a,beta-4,5,6,6a,beta-hexahydro-4beta-nitromethyl-5alpha-acetyl-2-oxo-2H-cyclopenta [b] furan.

EXAMPLE 7

3,3a,beta-4,5,6,6a,beta-hexahydro-4beta-nitromethyl-5alpha-acetoxy-2-oxo-2H-cyclopenta [b] furan To a solution of 13 g. of trifluoroperacetic acid in 100 ml. of methylene chloride was added 63 g. of disodium phosphate. To the resulting mixture was then added a solution of 12 g. of 3,3a,beta-4,5,6,6a,beta-hexahydro-4beta-nitromethyl-5alpha-acetyl-2-oxo-2H-cyclopenta [b] furan dissolved in 100 ml. of methylene chloride. The mixture was stirred for 8 hours after which time a second addition of 13 g. of trifluoroperacetic acid in 100 ml. of methylene chloride was added together with 63 g. of disodium phosphate. The mixture was stirred for an additional 12 hours after which time the reaction was poured into 500 ml. of ice water. The resulting mixture was then extracted with ethyl acetate, the organic extract washed with a 5% by weight sodium bicarbonate aqueous solution and then dried (MgSO₄). The solvent was then removed under reduced pressure and the residue triturated with diethyl ether to give 3,3a,beta-4,5,6,6a,beta-hexahydro-4beta-nitromethyl-5alpha-acetoxy-2-oxo-2H-cyclopenta [b] furan; m.p. 98°-101° centigrade.

EXAMPLE 8

3,3a,beta-4,5,6,6a,beta-hexahydro-4beta-nitromethyl-5alpha-hydroxyl-2-oxo-2H-cyclopenta [b] furan To a suspension of 7.5 g. of 3,3a, beta-4,5,6,6a,beta-hexahydro-4beta-nitromethyl-5alpha-acetoxy-2-oxo-2H-cyclopenta [b] furan in 20 ml. of dry methanol at 0° centigrade was added 28 ml. of a 2.2 molar solution of lithium methoxide in methanol. After stirring for 1 hour, the solution was treated with 1N-aqueous sulfuric acid to pH 3 and the methanol removed under reduced pressure. The residue was then extracted with ethyl acetate and the solution dried (MgSO₄). The solvent was then removed under reduced pressure and the residue triturated with diethyl ether to give 3,3a,beta-4,5,6,6a,beta-hexahydro-4beta-nitromethyl-5alpha-hydroxyl-2-oxo-2H-cyclopenta [b] furan, m.p. 79°-81° centigrade.

EXAMPLE 9

3,3a,beta-4,5,6,6a,beta-hexahydro-4beta-nitromethyl-5alpha-tetrahydropyranyloxy-2-oxo-2H-cyclopenta [b] furan To a suspension of 3.44 g. of 3,3a,beta-4,5,6,6a,beta-hexahydro-4beta-nitromethyl-5alpha-hydroxyl-2-oxo-2H-cyclopenta [b] furan in 60 ml. of dry benzene was added 2.4 ml. of dihydropyran and 50 mg. of p-toluenesulfonic acid. The mixture was stirred for 2 hours at room temperature and then washed with a 5% by weight aqueous sodium bicarbonate solution. The benzene solution was dried (MgSO₄) and the solvent and excess dihydropyran removed under high vacuum to give 4.9 g. of 3,3a,beta-4,5,6,6a,beta-hexahydro-4beta-nitromethyl-5alpha-tetrahydropyranyloxy-2-oxo-2H-cyclopenta [b] furan.

EXAMPLE 10

3,3a,beta-4,5,6,6a,beta-hexahydro-4beta-formyl-5alpha-tetrahydropyranyloxy-2-oxo-2H-cyclopenta [b] furan To a solution of 12.1 g. of 3,3a,beta-4,5,6,6a,beta-hexahydro-4beta-nitromethyl-5alpha-tetrahydropyranyloxy-2-oxo-2H-cyclopenta [b] furan in 150 ml. of dry methanol was added 19.4 ml. of a 2.4 molar solution of lithium methoxide in methanol. After 10 minutes, the solvent was removed under high vacuum and the residual aci-nitro salt dried for an additional 1.5 hours. The dried salt was then dissolved in 175 ml. of a saturated aqueous sodium tetraborate solution and cooled to 0° centigrade. A solution of 5.54 g. of sodium permanganate in 65 ml. of water was then added dropwise over a 5 minute period. The mixture was stirred an additional 10 minutes, treated with 200 ml. of a 1:4 parts by volume acetone-methylene chloride solution and then filtered through a bed of celite. The celite was washed with an additional 100 ml. of 1:4 parts by volume acetone-methylene chloride solution and the organic layers combined and dried (Na₂SO₄). The solvent was removed under pressure to give 3,3a,beta-4,5,6,6a,beta-hexahydro-4beta-formyl-5alpha-tetrahydropyranyloxy-2-oxo-2H-cyclopenta [b] furan.

EXAMPLE 11

3,3a,beta-4,5,6,6a,beta-hexahydro-4beta-(3-oxo-1-trans-octenyl)-5alpha-tetrahydropyranyloxy-2-oxo-2H-cyclopenta [b] furan To a suspension of 0.5 g. of sodium hydride in 150 ml. of dry glyme was added 4.7 g. of dimethyl (2-oxoheptyl)-phosphonate. After stirring for 1.5 hours, 4.9 g. of 3,3a,beta-4,5,6,6a,beta-hexahydro-4beta-formyl-5alpha-tetrahydropyranyloxy-2-oxo-2H-cyclopenta [b] furan dissolved in 25 ml. of glyme was added dropwise at 0° centigrade. After stirring for 3 hours at room temperature, 500 ml. of diethyl ether was added and the mixture washed with water. The organic layer was then dried (Na₂SO₄) and the solvent removed under reduced pressure. The residue was then washed through 60 g. of silica gel (pH 7) to give 6 g. of 3,3a,beta-4,5,6,6a,beta-hexahydro-4beta-(3-oxo-1-trans-octenyl)-5alpha-tetrahydropyranyloxy-2-oxo-2H-cyclopenta [b] furan.

EXAMPLE 12

3,3a,beta-4,5,6,6a,beta-hexahydro-4beta-(3-hydroxy-1-trans-octenyl)-5alpha-tetrahydropyranyloxy-2-oxo-2H-cyclopenta [b] furan To a solution of 5 g. of 3,3a,beta-4,5,6,6a,beta-hexahydro-4beta(3-oxo-1-trans-octenyl)-5alpha-tetrahydropyranyloxy-2-oxo-2H-cyclopenta [b] furan in 50 ml. of glyme was added excess zinc borohydride in 50 ml. of glyme and the resulting solution stirred at room temperature for 3 hours. The solution was then cooled to 0° centigrade and treated with 200 ml. of water, 400 ml. of ether and 10 ml. of 0.5N aqueous sulfuric acid. The ether layer was separated and dried (MgSO₄) and the solvent was removed under reduced pressure to give 3,3a,beta-4,5,6,6a,beta-hexahydro-4beta-(3-hydroxy-1-trans-octenyl)-5alpha-tetrahydropyranyloxy-2-oxo-2H-cyclopenta [b] furan.

EXAMPLE 13

3,3a,beta-4,5,6,6a,beta-hexahydro-4beta-(3alpha-hydroxy-1-trans-octenyl)-5beta-hydroxy-2-oxo-2H-cyclopenta [b] furan To a 2:1 parts by volume acetic acid-water solution (50 ml.) was added 2 g. of 3,3a,beta-4,5,6,6a,beta-hexahydro-4beta-(3-hydroxy-1-trans-ocetnyl)-5beta-tetrahydropyranyloxy-2-oxo-2H-cyclopenta [b] furan. The solution was heated at 40° centigrade for 2.5 hours after which time the acetic acid was neutralized with solid potassium bicarbonate. The resulting mixture was then extracted several times with ethyl acetate and the organic solution dried (MgSO$_4$). The solvent was then removed under reduced pressure and the residue chromatographed on silica gel to give 3,3a,beta-4,5,6,6a,-beta-hexahydro-4beta-(3alpha-hydroxy-1-trans-octenyl)-5beta-hydroxy-2-oxo-2H-cyclopenta [b] furan. Also obtained by chromatography was the 3,3a,-beta-4,5,6,6a,beta,hexahydro-4beta-(3beta-hydroxy-1-trans-octenyl)-5beta-hydroxy-2-oxo-2H-cyclopenta [b] furan.

We claim:
1. A compound of the formula:

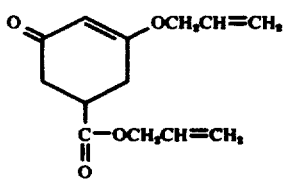

* * * * *